US00PP17121P2

(12) United States Plant Patent
Suzuki et al.

(10) Patent No.: US PP17,121 P2
(45) Date of Patent: Oct. 3, 2006

(54) ***VERBENA* PLANT NAMED 'SUNMARICORAPI2 '**

(50) Latin Name: *Verbena×hybrida*
Varietal Denomination: Sunmaricorapi2

(75) Inventors: Kenichi Suzuki, Osaka (JP); Takeshi Kanaya, Shiga (JP); Yasunori Yomo, Kanagawa (JP); Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 253 days.

(21) Appl. No.: 11/041,622

(22) Filed: Jan. 22, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—C. A. Whealy

(57) ABSTRACT

A new and distinct cultivar of *Verbena* plant named 'Sunmaricorapi2', characterized by its decumbent plant habit; freely branching habit; dense and bushy growth habit; attractive red purple-colored flowers; freely and continuous flowering habit; long-lasting flowers; non-fertile flowers; and good garden performance.

1 Drawing Sheet

Botanical designation: *Verbena×hybrida.*
Cultivar denomination: 'Sunmaricorapi2'.

BACKGROUND OF THE INVENTION

The present Invention relates to a new and distinct cultivar of *Verbena* plant, botanically known as *Verbena× hybrida,* and hereinafter referred to by the cultivar name Sunmaricorapi2.

The new *Verbena* is a naturally-occurring whole plant mutation of the *Verbena×hybrida* cultivar Sunmariripi, disclosed in U.S. Plant Pat. No. 11,037. The new *Verbena* was selected by the Inventors as a flowering plant within a population of plants of the parent cultivar in a controlled environment in Yokaichi, Shiga, Japan in March, 1999.

Asexual reproduction of the new cultivar by terminal cuttings at Yokaichi, Shiga, Japan since November, 1999, has shown that the unique features of this new *Verbena* are stable and reproduced true to type in successive generations.

SUMMARY OF THE INVENTION

Plants of the cultivar Sunmaricorapi2 have not been observed under all possible environmental conditions. The phenotype may vary somewhat with variations in environment such as temperature and light level without, however, any variance in genotype.

The following traits have been repeatedly observed and are determined to be the unique characteristics of 'Sunmaricorapi2'. These characteristics in combination distinguish 'Sunmaricorapi2' as a new and distinct cultivar of *Verbena:*

1. Decumbent plant habit.
2. Freely branching habit; dense and bushy growth habit.
3. Attractive red purple-colored flowers.
4. Freely and continuous flowering habit.
5. Long-lasting flowers.
6. Non-fertile flowers
7. Good garden performance.

Plants of the new *Verbena* are most similar to plants of the parent, the cultivar Sunmariripi. In side-by-side comparisons conducted in Yokaichi, Shiga, Japan, plants of the new *Verbena* differed from plants of the cultivar Sunmariripi in the following characteristics:

1. Plants of the new *Verbena* were more compact than plants of the cultivar Sunmariripi.
2. Plants of the new *Verbena* had smaller inflorescences than plants of the cultivar Sunmariripi.
3. Plants of the new *Verbena* and the cultivar Sunmariripi differed in flower coloration.
4. Plants of the new *Verbena* were not fertile and did not produce seed whereas plants of the cultivar Sunmariripi produced seed.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Verbena.*

The photograph at the top of the sheet is a side perspective view of a typical plant of 'Sunmaricorapi2'.

The photograph at the bottom of the sheet is a close-up view of typical flowers and leaves of 'Sunmaricorapi2'.

DETAILED BOTANICAL DESCRIPTION

The aforementioned photographs, following observations and measurements describe plants grown in Yokaichi, Shiga, Japan in an outdoor nursery and under commercial production practices. Plants were grown in 15-cm containers and were about four months old when the photographs and description were taken. During the production of the plants, day temperatures averaged 22° C. and night temperatures averaged 12° C. Plants were pinched one time in the summer. In the following description, color references are made to The Royal Horticultural Society Colour Chart, 2001 Edition, except where general terms of ordinary dictionary significance are used.

Botanical classification: *Verbena drummondii* cultivar Sunmaricorapi2.

Parentage: Naturally-occurring whole plant mutation of the *Verbena×hybrida* cultivar Sunmariripi, disclosed in U.S. Plant Pat. No. 11,037.

Propagation:

*Type*.—By terminal cuttings.

*Time to initiate roots*.—About 10 to 14 days at 20 to 25° C.

*Time to produce a rooted plant*.—About one month at 20 to 25° C.

*Root description*.—Fine, fibrous, fleshy; ivory to pale brown in color.

*Rooting habit*.—Freely branching.

Plant description:

*Plant form/habit*.—Decumbent plant habit; broadly inverted triangle; vigorous growth habit. Freely branching habit with short internodes, dense and bushy growth habit.

*Plant height*.—About 8.3 cm.

*Plant width* (*spread*).—About 46.2 cm.

*Lateral branches*.—Length: About 25 cm. Diameter: About 2.3 mm. Internode length: About 2.5 cm. Strength: Strong. Texture: Pubescent. Color: 144A; longitudinal stripes, 200A.

*Foliage description*.—Arrangement: Opposite, simple; sessile. Length: About 3.9 cm. Width: About 3.1 cm. Shape: Broadly ovate. Apex: Acute. Base: Obtuse. Margin: Crenate to serrate. Texture, upper and lower surfaces: Pubescent. Venation pattern: Pinnate; reticulate. Color: Developing leaves, upper surface: 137B. Developing leaves, lower surface: 138B. Fully expanded leaves, upper surface: 137A. Fully expanded leaves, lower surface: 138B.

Flower description:

*Flower type/habit*.—Single, star-shaped salverform flowers arranged in umbels; flowers face mostly upright. Freely flowering habit with about nine open flowers per inflorescence.

*Fragrance*.—None detected.

*Natural flowering season*.—Continuously flowering from April to November in Japan. Flowers not persistent.

*Postproduction longevity*.—Flowers last about one week on the plant.

*Inflorescence height*.—About 2.4 cm.

*Inflorescence diameter*.—About 6 cm.

*Flower buds*.—Height: About 1.1 cm. Diameter: About 2.3 mm. Shape: Cylindrical. Color: N57A.

*Flowers*.—Diameter: About 1.8 cm. Depth: About 2.1 cm.

*Petals*.—Quantity per flower: Typically five in a single whorl; petals fused at the base into a narrow tube. Lobe length: About 7.6 cm. Lobe width: About 6.5 mm. Shape: Cordate. Apex: Emarginate. Margin: Entire. Aspect: Mostly flat. Texture, upper and lower surfaces: Smooth, glabrous; satiny. Color: Developing petals, upper surface: N57A. Developing petals, lower surface: 62B. Fully expanded petals, upper surface: 58B. Fully expanded petals, lower surface: 62B.

*Sepals*.—Quantity per flower: Typically five in a single whorl, fused; narrow tubular calyx. Calyx length: About 1.1 cm. Calyx diameter: About 2 mm. Shape: Lanceolate. Apex: Acute. Texture, upper and lower surfaces: Smooth, glabrous. Color, upper and lower surfaces: 144A; longitudinal lines, 200A.

*Peduncles*.—Length: About 3.5 cm. Diameter: About 1.3 mm. Color: 146B.

*Reproductive organs*.—Stamens: Quantity per flower: Typically four. Anther shape: Linear. Anther length: About 0.9 mm. Anther color: 154B. Pollen amount: Moderate. Pollen color: 1B. Pistils: Quantity per flower: Typically one. Pistil length: About 1.5 cm. Stigma shape: Bi-parted. Stigma color: 144A. Style length: About 1.3 cm. Style color: 144B. Ovary color: 145B.

*Seed/fruit*.—Seed and fruit development have not been observed.

Disease/pest resistance: Plants of the new *Verbena* have not been noted to be resistant to specific pathogens and pests common to *Verbena*.

Garden performance: Plants of the new *Verbena* have been observed to have good garden performance and tolerate rain, wind and tolerated temperatures from 0 to 35° C.

It is claimed:

1. A new and distinct cultivar of *Verbena* plant named 'Sunmaricorapi2', as illustrated and described.

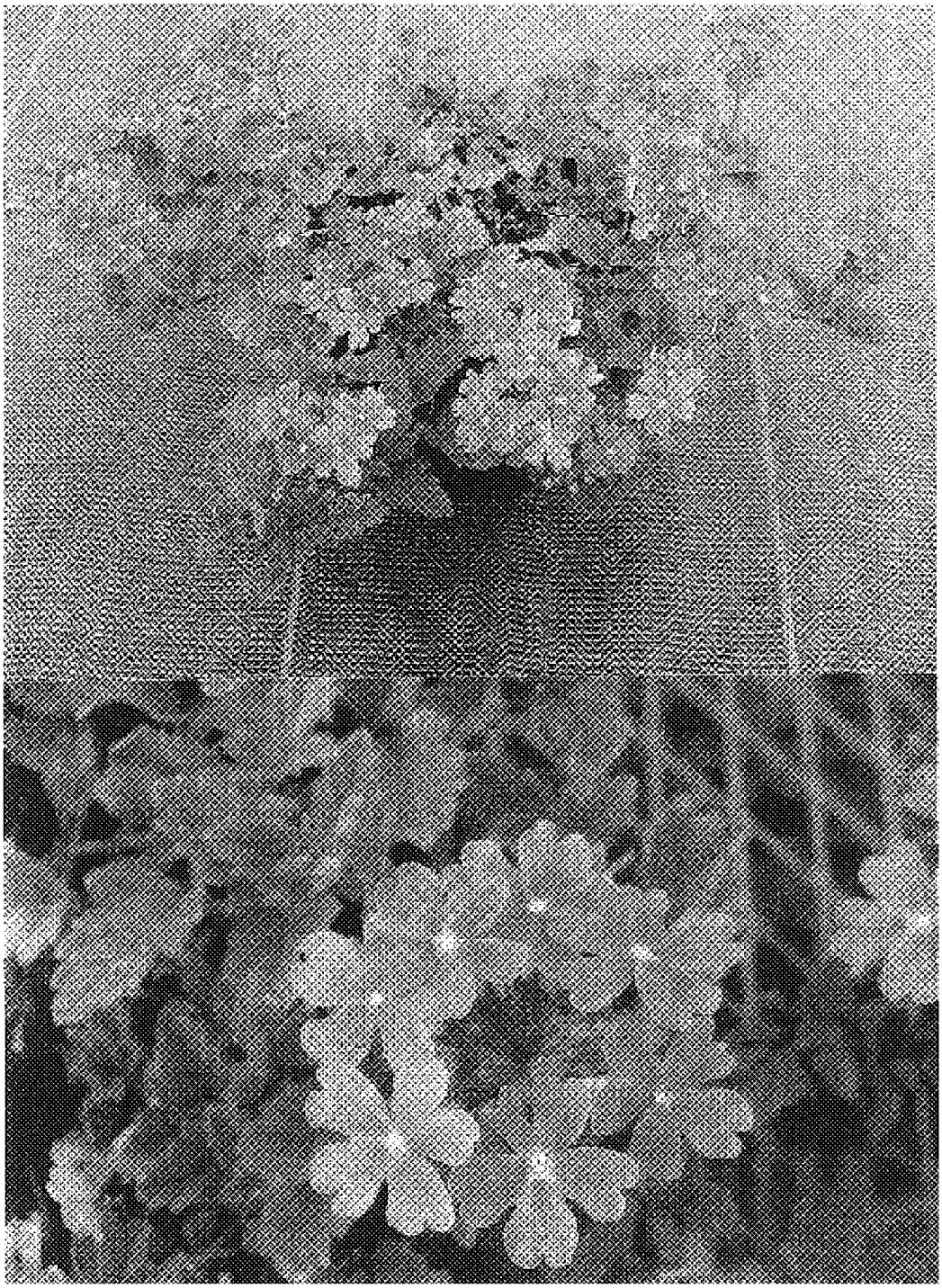

* * * * *